United States Patent [19]

Belanger et al.

[11] Patent Number: 4,536,515
[45] Date of Patent: Aug. 20, 1985

[54] SUBSTITUTED PHENYLALKENOIC ACIDS AND ESTERS

[75] Inventors: Patrice C. Belanger, Dollard des Ormeaux; John W. Gillard, Pointe Claire, both of Canada

[73] Assignee: Merck Frosst Canada, Inc., Quebec, Canada

[21] Appl. No.: 446,908

[22] Filed: Dec. 6, 1982

[51] Int. Cl.$^3$ .................. C07L 69/76; A01N 37/00
[52] U.S. Cl. .................. 514/532; 514/541; 514/568; 514/570; 514/576; 548/532; 549/230; 260/465 K; 562/459; 562/492; 560/51; 560/59; 560/102
[58] Field of Search ............... 562/492, 459; 560/102, 560/51, 59, 492; 514/532, 541, 570, 576; 548/532; 549/230

[56] References Cited

U.S. PATENT DOCUMENTS 3,859,338  1/1975  Engel et al. .................. 562/492

FOREIGN PATENT DOCUMENTS 825643   8/1971   Belgium .
840354  10/1976   Belgium .
0020230 10/1980   European Pat. Off. ............ 562/492
20230   12/1980   European Pat. Off. .
2205732  8/1973   Fed. Rep. of Germany .
847779   9/1960   United Kingdom .

OTHER PUBLICATIONS

Morand et al., J. Pharm. Sci. 53, 504–508, (1964).
Child et al., Arzniem., Foych., (1980), 30 (1), 695, 699.
Franke, A. et al., Helvetica Chimica Acta, vol. 58, pp. 278–83, 1975.

Primary Examiner—Paul J. Killos
Attorney, Agent, or Firm—Alice O. Robertson; Daniel T. Szura

[57] ABSTRACT

Substituted phenylalkenoic acids and esters of the formula:

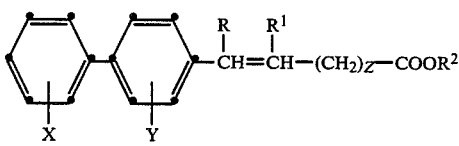

having useful pharmaceutical activity are disclosed.

11 Claims, No Drawings

SUBSTITUTED PHENYLALKENOIC ACIDS AND ESTERS

BACKGROUND OF THE INVENTION

The present invention is concerned with certain 6-biphenylylalkenoic acids and esters having pharmaceutical utility, especially for inhibiting blood platelet aggregation.

Biphenylylalkenoic acids where the alkenoic acid moiety has four or less carbon atoms are known (see e.g. European Patent Application No. 20230, German No. 2,205,732, RD No. 189,021, Belgian No. 840,354, Belgian No. 825,643). These compounds are generally taught to have anti-inflammatory activity. 2-(4-biphenylyl)-4-hexenoic acid of the formula

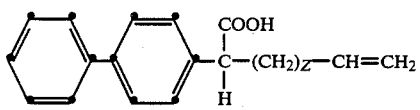

is disclosed in Morand et al., J. Pharm. Sci. 53, 504–507 (1964); and is taught to inhibit cholesterol synthesis.

A class of biphenylylakenoic acids have been discovered. These hexenoic acids are useful as anti-inflammatory agents, as blood platelet aggregation inhibitors and to prevent bronchoconstriction.

SUMMARY OF THE INVENTION

Biphenylylhexenoic acids and esters of the formula:

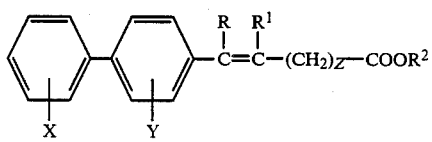

and their use as pharmaceuticals.

DETAILED DESCRIPTION OF THE INVENTION

The invention is embodied in compounds having the formula

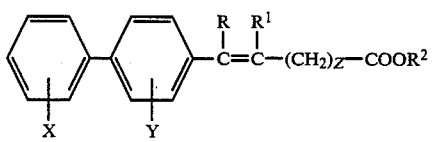  I wherein
R is H or $C_1$–$C_4$ alkyl, $C_1$–$C_4$ alkoxy or hydroxy,
$R^1$ is H or $C_1$–$C_4$ alkyl, $C_1$–$C_4$ alkoxy or hydroxy,
$R^2$ is
 (i) hydrogen,
 (ii) $C_1$–$C_6$ alkyl,

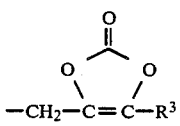

wherein $R^3$ is $C_1$–$C_6$ alkyl or aryl (as defined in U.S. Pat. No. 4,342,693) or
(iv)

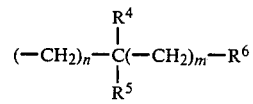  III wherein
 n is 0, 1, 2, or 3;
 m is 0, 1, 2, or 3;
 $R^4$ and $R^5$ are individually H or alkyl of 1 to 3 carbon atoms and;
 $R^6$ is selected from the group consisting of
  (A) a monocyclic or bicyclic heterocyclic radical containing from 3 to 12 nuclear carbon atoms and 1 or 2 nuclear hetero atoms selected from N and S with at least one being N, and with each ring in the said heterocyclic radical containing 5 to 6 members and
  (B) the radical $X^1$—$R_7$
   wherein $X^1$ is —O—, —S— or —NH— and $R^7$ contains up to 21 carbon atoms and is (1) a hydrocarbon radical or (2) an acyl radical of an organic acyclic or monocyclic carboxylic acid containing not more than 1 hetero atom in the ring,
Y is H, halo, hydroxy, $C_1$–$C_4$ alkoxy or azido,
X is H, halo, hydroxy, $C_1$–$C_4$ alkoxy or azido, and
Z is 3, 5 or 7,
and pharmaceutically acceptable salts thereof. A preferred definition of Z is 3.

The formula I compounds exist as geometrical isomers by virtue of the alkene double bond. Thus, formula I includes mixtures of these isomers as well as the individual isomers. The isomers are conventionally designated as e.g. cis and trans.

The pharmaceutically acceptable salts are salts of the formula I acids with suitable bases, exemplified by the ammonium salts, the alkali metal salts e.g., sodium, potassium, the alkaline earth metal salts e.g. Ca, Mg and salts with amines such as lysine, morpholine, piperazine and the like.

Identification and introduction of the formula II ester group is taught in U.S. Pat. No. 4,342,693 whose disclosure, to the extent necessary, is incorporated herein by reference. A preferred method for preparing a formula II group ester is by treating the lithium or silver salt of the formula I acid with the bromo derivative:

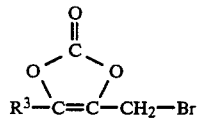

in a suitable reaction medium. Methyl t-butyl and phenyl are preferred $R^3$ definitions.

Identification and introduction of the formula III ester group is taught in U.S. Pat. No. 3,983,138 and U.S. Pat. No. 3,988,341 and, to the extent necessary, these disclosures are incorporated herein by reference. Preferred formula III ester groups are those where $R^6$ is (i) $X^1$—$R^7$ where $X^1$ is O, S or NH and $R^7$ is hydrocarbyl or non-heterocyclic acyl or (ii) glutarimido, nicotinamido, phthalimido, naphthalimido, acetamido, maleimido or succinimido.

More preferred formula III ester groups are those having the formula: $-CH_2-R^8$, $-CH(CH_3)-R^8$ or $-(CH_2)_2-R^8$ where $R^8$ is

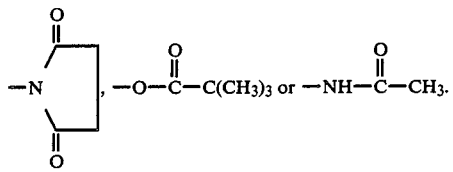

The $C_1-C_4$ alkyl group substituents are exemplified by $CH_3$, t-butyl, isopropyl and the like. The $C_1-C_6$ alkyl group substituents are exemplified by $CH_3$, n-hexyl, sec.-butyl and the like. The halo substituent is Cl, Br, or F.

The $C_1-C_4$ alkoxy groups are exemplified by methoxy, ethoxy, isopropoxy, t-butoxy and the like.

Preferred compounds are those of formula I where $R^2$ is H. A more preferred group of compounds is formula I where $R_2$ is H and $R/R^1$ are independently selected from H and $CH_3$.

Another more preferred group of compounds is formula I where R, $R^1$ and $R^2$ are all H and Z is 3. A most preferred compound is formula I where X, Y, R, $R^1$ and $R^2$ are all H and Z is 3.

The compounds of Formula I are useful as pharmaceuticals.

Representative compounds inhibit bronchoconstriction induced by leukotrienes ($LTD_4$) or arachidonic acid—and in the latter instance, show no inhibition of the concomitant fall in blood pressure due to inhibition of synthesis prostaglandin $I_2$ and $F_2$. Thus, the present compounds are considered to have thromboxane synthetase (TS) enzyme and cyclooxygenase (CO) enzyme inhibiting properties. A discussion of the metabolic cycle involving these enzymes is found in U.S. Pat. No. 4,233,778.

By virtue of the pharmacological activities of the formula I compounds, they are useful e.g. as anti-inflammatory agents, as cardiovascular agents, e.g., to treat and prevent blood platelet aggregation and to treat asthma.

For use as blood platelet aggregation inhibitors the present compounds are administered either orally or parenterally in daily dosages ranging fr m 5 mg. to 500 mg.

For use as anti-inflammatory agents, the present compounds are administered orally or parenterally in daily dosages ranging from 10 mg. to 1,500 mg.

For use in treating asthma, the present compounds are administered orally, parenterally or by insufflation. The oral or parenteral daily dosage will range from 50 mg. to 1,500 mg. Administration by insufflation e.g., spray, will be in metered doses ranging from 50 to about 1000 mcg, administered as needed.

Appropriate dosage forms will be used. Suitable oral dosage forms are tablets, elixirs, solutions, emulsions, capsules and the like. Suitable parenteral dosage forms are solutions, emulsions and the like. Suitable insufflation dosage forms are sprays, aerosols, and the like. The dosage forms are prepared using conventional procedures and, where required, pharmacologically acceptable diluents, carriers and the like.

The compounds of formula I can be prepared by any convenient method.

One such process involves the reaction of a biphenylyl aldehyde with a triphenyl phosphine alkanoic acid adduct in the presence of a coupling agent such as BuLi/hexamethyl disilazane or $K_2CO_3$/18-Crown-6, as illustrated by the following equation:

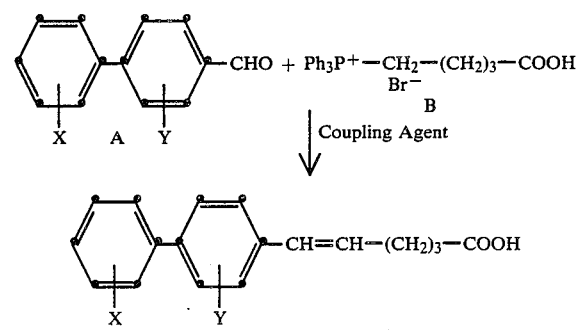

This reaction is generally carried out in a suitable solvent such as tetrahydrofuran or a like aprotic solvent at below 0° C. and preferably about $-50°$ to $-80°$ C.

Another process for preparing compounds of Formula I is by dehydrating an appropriate hydroxy derivative, as illustrated by the following equation:

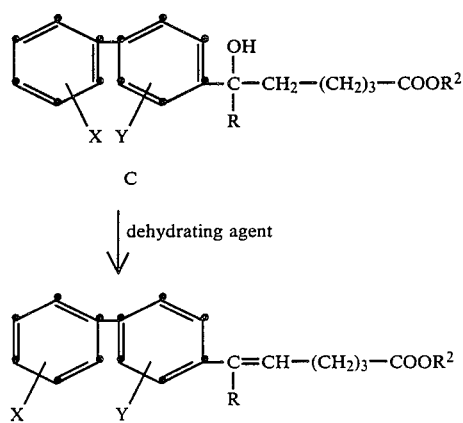

Any conventional dehydrating agent can be used for example p-toluenesulfonic acid (p-TsOH) and the like. Generally, the reaction is carried out in a liquid reaction medium such as an inert aromatic hydrocarbon.

The formula C precursor is prepared from the corresponding ketone derivative as illustrated by the following equations.

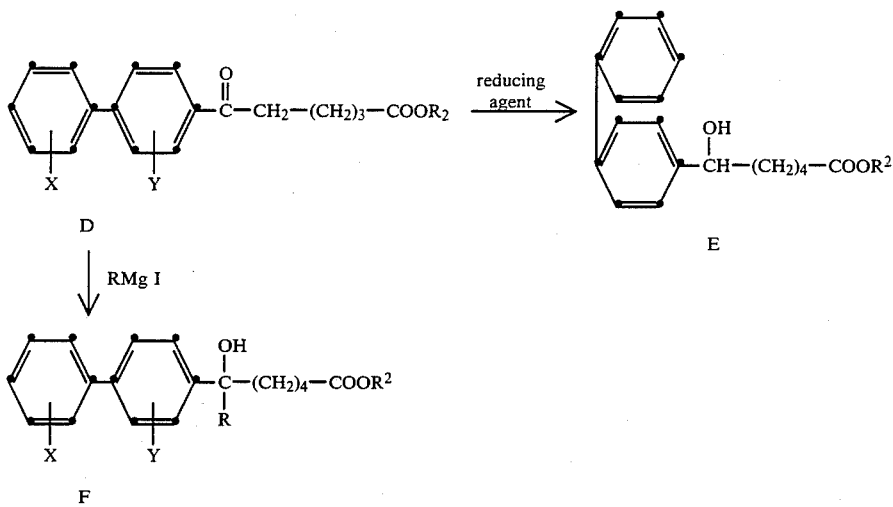

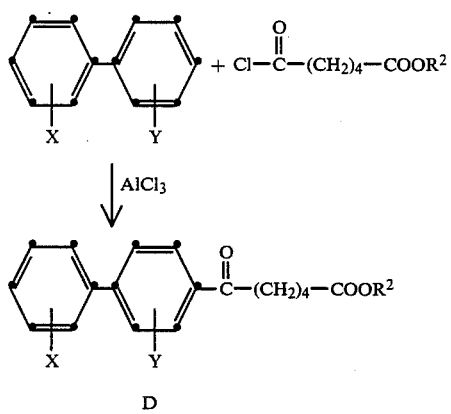

For preparing formula E, conventional reducing agents/reaction conditions are used. Conventional Grignard reactants/conditions are used to prepare formula F.

The preparation of precursor D involves conventional Friedel Crafts coupling of a biphenyl with an appropriate acyl halide as illustrated by the following equation:

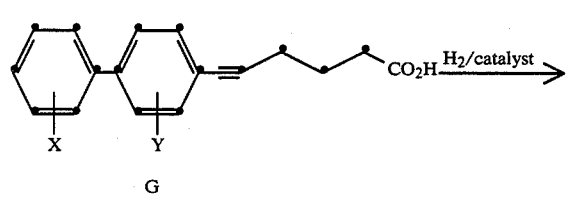

Esters of Formula I are prepared from the free acid (where $R^2$ is H) using conventional esterification procedures e.g. diazomethane in a suitable solvent, or an alcohol with an acid catalyst.

A third process for preparing compounds of Formula I, in particular those with the cis configuration of the double bond in the hexenoic acid chain, involves the selective reduction of an appropriate biphenylyl hexynoic acid, as illustrated by the following equation:

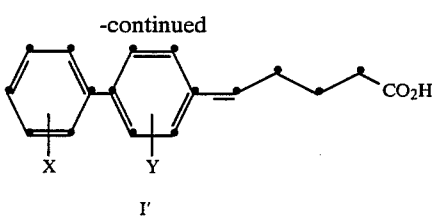

-continued

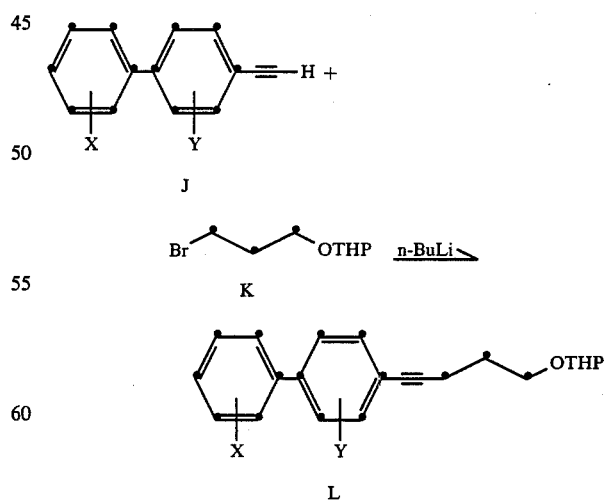

A typical reduction was effected using Lindlar catalyst at a pressure of 10–60 psi $H_2$ in an alcohol solvent such as methanol or ethanol.

The appropriate alkynoic acid G is prepared by a series of steps involving alkylation of appropriately substituted biphenylyl acetylene J, catalyzed by a strong base such as a BuLi in an ether solvent such as THF, with a tetrahydropyranyl protected bromo propanol K, as illustrated by the following equation:

The protected alcohol L is converted directly or sequentially to the nitrile H using conventional procedures, and the nitrile is then hydrolyzed to obtain G, as illustrated by the following equation:

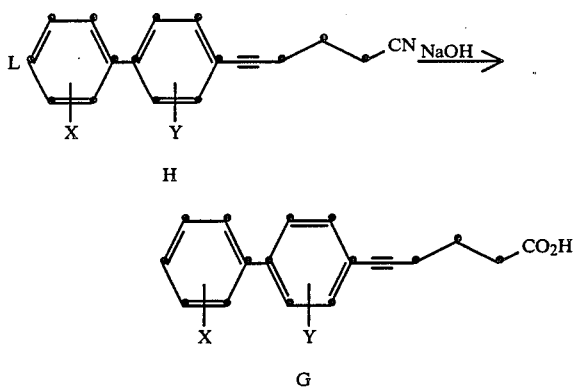

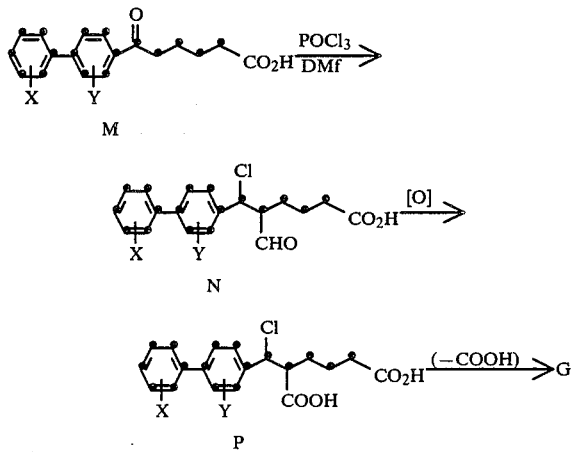

The G compound may also be prepared by reacting J with an appropriate terminally substituted carboxylic acid such as 4-bromobutanoic acid or equivalent.

A fourth process for the preparation of biphenyl alkynoic acids involves the following new procedure.

A Vilsmeir reaction is performed on an appropriate phenyl ketone using the known phosphorous oxychloride/dimethyl formamide method. The chloro-formyl derivative N so formed is oxidized using the common oxidizer sodium chlorate in aqueous buffer pH3–6 and the so formed chloro-acid P is decarboxylated e.g., in the presence of a Cu powder and a basic solvent like quinoline at a temperature between 100° and 160° C. yielding the intermediate alkynoic acid G. This intermediate G can then be converted as described above to the Formula I compound.

The following examples illustrate the preparation of compounds of Formula I. All temperatures are in °C.

A. WITTIG APPROACHES TO 6-BIPHENYLYLHEX-5-ENOIC ACIDS

EXAMPLE 1

6-(4'-Biphenylyl)hex-5-enoic Acids

Six grams biphenylcarboxaldehyde, 10.23 g 5-carboxypentyl triphenylphosphorane bromide, 5.8 g anhydrous $K_2CO_3$ and 130 mg 18-Crown-6 were suspended in 240 mL dry tetrahydrofuran. The mixture was heated and stirred at reflux for 7 days, diluted with 200 mL $H_2O$, extracted with EtOAc (5×200 mL). The EtOAc extract was dried ($Na_2SO_4$) and concentrated, the residue was taken up in methanol (200 mL) treated with 1 equivalent $BF_3.OEt_2$ and the methyl esters of the cis and trans acids separated by chromatography (yield 59%). The esters were hydrolyzed upon dissolving in MeOH (100 mL) and treatment with 1N NaOH (50 mL). Acidification resulted in precipitation of the corresponding acids cis-6-(4'-biphenyl)hex-5-enoic acid, m.p. 107°–109° and trans-6-(4'-biphenylyl)hex-5-enoic acid, m.p. 116°–118°.

EXAMPLE 2

6-(4''-Fluoro-4'-biphenylyl)hex-5-enoic Acids

Six grams 4'-fluoro-4-biphenylyl carboxaldehyde, 10.2 g 5-carboxypentyl triphenyl phosphorane bromide, and 5.8 g anhydrous $K_2CO_3$, 130 mg 18-crown-6 were suspended in anhydrous THF and refluxed for 7 days. The solution was diluted with 200 mL $H_2O$, and extracted with EtOAc (5×100 mL). The dried organic phases were concentrated and methylated as in Example 1 with $BF_3.OEt_2$ in methanol. Separation of the cis and trans isomers was effected by HPLC, yield 45%. Hydrolysis was achieved using NaOH (1N) in methanol followed by acidification to precipitate the products, cis-6-(4'-fluoro-4-biphenylyl)hex-5-enoic acid m.p. 115°–116° and trans-6-(4'-fluoro-4-biphenylyl)hex-5-enoic acid m.p. 128°–130°.

B. FRIEDEL-CRAFTS ACYLATION TO 6-KETO-6-(4'-BIPHENYLYLHEXANOIC ACIDS

Example 3

6-(4'-Biphenylyl)-6-keto-hexanoic acid 2

Seventeen grams biphenyl was added at 0° to a solution containing tetrachloroethane (250 mL), $AlCl_3$ (28.4 g) and methyl-5-chloroformyl pentanoate (20 g). After 10 minutes, the reaction was poured onto ice and filtered to yield 30.3 g, (94%) methyl-6-(4'-biphenylyl)-6-keto hexanoate. The acid 2 was recovered by hydrolysis of the ester with NaOH (1N) followed by acidification, m.p. 161°–162° (lit 159°–160°).

EXAMPLE 4

6-(4''-Fluoro-4'-biphenylyl)-6-keto hexenoic acid 3

Two grams 4'-fluorobiphenylyl was added to a solution containing 2.0 g methyl-5-(chloroformyl)pentanoate, 3.0 g $AlCl_3$ and 200 mL methylene chloride. After 15 minutes stirring at 0°, the solution was kept at 15°–20° for 16 hours. The reaction was poured into ice and the product 3 was filtered and recrystallized from MeOH (2.0 g 55%). Hydrolysis was achieved by stirring the ester with 20 mL 1N NaOH in 50 mL methanol. Acidification precipitated the product 3, m.p. 182°–184°.

EXAMPLE 5

6-[4''-Methoxy-(4'-biphenyl)]-6-keto Hexanoic Acid 4

Two grams 4'-methoxybiphenyl was added to a solution containing 200 mL dichloroethane, 2.0 g methyl-5-(chloroformyl)pentanoate and 3.0 g $AlCl_3$ at −10° C. The reaction was stirred at −10° for 15 minutes poured onto ice and the product precipitated. Hydrolysis in 1N NaOH, followed by acidification, precipitated the acid 4 in 67% yield m.p. 184°–186°. Other 6-ketonexanoic acids prepared using the process illustrated in Example 5 were 6-[4''-methyl-(4'-biphenyl)] 6-keto hexanoic acid, m.p. 143°–145°, 6-[4''-carboxyl-(4'-biphenyl)]-6-keto hexanoic acid, m.p. 270° (decomp.) and 6-[4''- hydroxy(4'-biphenyl)]-6-keto hexanoic acid, m.p. 116°–119°.

C. GENERAL PROCEDURE FOR GRIGNARD CONVERSION OF 6-KETO BIPHENYLYL HEXANOIC ACIDS

EXAMPLE 6

The esters, methyl-6-(4"-fluoro-4'-biphenylyl)-6-keto hexanoate, methyl-6-(4'-biphenylyl)-6-keto hexanoate, methyl-6-(4"-methoxy 4'-biphenylyl)-6-keto hexanoate and methyl-6-(4"-methyl-4'-biphenylyl)-6-keto hexanoate, were respectively dissolved in toluene at −40°. A molar equivalent of the respective Grignard reagent was added (methyl or ethyl magnesium bromide) in THF (3M) dropwise. THe reaction mixtures were stirred at RT overnight. The organic phases were then diluted with EtOAc (2×V) and extracted with $H_2O$. The organic phase was dried ($Na_2SO_4$) and concentrated. Products were isolated by chromatography on silica gel (EtOAc/hexane 3:7). Hydrolysis to the free acid was achieved by treating the esters from the above Grignard reactions with methanol (5% w/v) and adding 5 equivalents of 0.1N NaOH. Acidification resulted in precipitation. The following products were thus obtained and characterized: 6-(4'-biphenylyl)-6-hydroxy hexanoic acid, m.p. 77°–80°; 6-(4"-fluoro-4'-biphenylyl)-6-methyl-6-hydroxy hexanoic acid, m.p. 48°–52°; 6-(4"-methyl-4'-biphenylyl)-6-methyl-6-hydrous hexanoic acid, m.p. 86°–88°.

The following products may be prepared using the processes described in Example 6: 6-(4"-methoxy-4'-biphenylyl)-6-methyl-6-hydroxy hexanoic acid and 6-(4"-fluoro-4'-biphenylyl)-6-ethyl-6-hydroxy hexanoic acid.

GENERAL PROCEDURE FOR REDUCTION OF SUBSTITUTED 6-KETO-6-(4'-BIPHENYL)HEXANOIC ACID ESTERS

Example 7

Forty grams 6-keto-6-(4'-biphenylyl)hexanoate methyl ester was dissolved in 370 mL MeOH. $NaBH_4$ 5.1 g was added portionwise at room temperature. The reaction was complete after 10 minutes. $H_2O$ was added (100 mL) and the solution concentrated to 200. The solution was extracted by $CH_2Cl_2$ to (3×200 mL). Purification was achieved by chromatography on silica gel.

Hydrolysis to the acid was achieved by treatment with 1N NaOH (30 mL) in MeOH (50 mL) and precipitation of the product with HCl. The following hexanoic acid products were thus obtained: 6-hydroxy-6-(4'-biphenylyl)hexanoic acid m.p. 260°; 6-hydroxy-6-(4"-fluorobiphenylyl)hexanoic acid, m.p. 175°–178°. Other products which may be obtained using the processes described in claim 7 are
6-hydroxy-6-(4'-hydroxybiphenylyl)hexanoic acid;
6-hydroxy-6-(4'-carboxybiphenylyl)hexanoic acid;
6-hydroxy-6-(4'-carbomethoxybiphenylyl)hexanoic acid.

E. GENERAL PROCEDURE FOR DEHYDRATION OF 6-HYDROXY-6-(4'-BIPHENYLYL)HEXANOIC ACIDS

EXAMPLE 8

The esters of 4"-substituted, 2'-substituted or 2',4"-disubstituted 6-hydroxy-6-(4'-biphenylyl)hexanoic acid (5 g) were dissolved in toluene (150 mL). Then 0.6 g p-toluene sulphonic acid was added. The solution was heated to reflux for 10 minutes. After evaporation to near dryness, water was added (25 mL) and the solution extracted with ethyl acetate. The product was purified by chromatography on silica gel and hydrolysis of the ester was achieved with 1N NaOH (50 mL) in MeOH 50 mL. Acidification (1N HCl) precipitated the product acid. The following hexenoic acids were thus prepared: trans-6-(4'-biphenylyl)hex-5-enoic acid, m.p. 129°–130°; trans-6-(4"-fluoro-4'-biphenylyl)hex-5-enoic acid, m.p. 128°–130°; trans-6-(4"-methoxy-4'-biphenylyl)hex-5-enoic acid, m.p. 111°–120°; trans-6-(4"-carboxy-4'-biphenylyl)hex-5-enoic acid, m.p. 196°–201°. The process of Example 8 may also be used to prepare products such as 6-[4"-methyl(4'-biphenylyl)]-hex-5-enoic acid and 6-[4"-methyl-2'-fluoro-4'-biphenylyl)]hex-5-enoic acid.

F. GENERAL PROCEDURE FOR DEHYDRATION OF 6-ALKYL-6-HYDROXY-6-(4'-BIPHENYLYL)HEXANOIC ACIDS

EXAMPLE 9

The esters of 6-alkyl-6-hydroxy-(4'-biphenylyl)hexanoic acid were dissolved (10 g) in toluene 200 mL and 1.1 g p-toluene sulphonic acid was added. The solution was heated to reflux for 10 minutes. After evaporation to dryness, addition of water (25 mL) and extraction of the aqueous with ethyl acetate, (5×50 mL) separation of the cis and trans isomers was achieved by high performance liquid chromatography on silica gel. Hydrolysis was achieved with 1N NaOH in MeOH. Acidification precipitated the product hexenoic acids. The following-6-(4'-biphenylyl)hept-6-enoic acid, m.p. 178°–180°; cis-6-(4'-biphenylyl)hept-6-enoic acid, m.p. 154°–156°; trans-6-(4"-fluoro-4'-biphenylyl)hept-6-enoic acid, m.p. 102°–105° and cis-6-(4"-fluoro-4'biphenylyl)hept-6-enoic acid, m.p. 132°–135°.

Analogous octenoic acids (where Z is 5 in Formula I) and decenoic acids (where Z is 7 in Formula I) are also prepared using appropriate starting materials in the Example 8 or 9 processes.

G. PROCEDURE FOR THE PREPARATION OF 6-(4'-BIPHENYL)-HEX-5-YNOIC ACID 10

EXAMPLE 10

Biphenyl acetylene 5.6 g was dissolved in THF (150 mL) at −78° C. One equivalent n-BuLi was added over one hour. The reaction was allowed to reach room temperature for one hour. 1-Iodo-3-O-tetrahydropyranylpropan-3-ol was added, (one equivalent). The reaction was refluxed for 24 hours. The product 1-O-tetrahydropyranyl-6-(4'biphenylyl)-pent-5-yn-1-ol, (oil C: 82.47, H: 7.55) was isolated by addition of water and extraction with ethyl acetate. The product (1 g) was dried (60° $10^{-3}$ mmHg), dissolved in $CH_2Cl_2$ (50 mL) and $Ph_3P.Br_2$ (1.95 g) was added, after stirring for 15 minutes at room temperature NaCN (0.54 g) in 20 mL DMSO was added. The mixture was heated at 45° for 16 hours. The intermediate 1-cyano-6-(4'-biphenylyl)-pent-5-yne m.p. 60°–61° C.: 88.13, H: 6.16, N: 5.71 was isolated by addition of water and extraction with EtOAc-hydrolysis to the title acid 10 was achieved by refluxing the nitrile in 10 mL (2 N NaOH in 50 mL ethanol) followed by acidification with 6 N HCl. The product 10 was filtered off and dried, 70% yield. m.p. 95°-96°.

H. PROCEDURE FOR THE PREPARATION OF 6-(4'-BIPHENYL) HEX-5-YNOIC ACID

EXAMPLE 11

(Step A) 6-4'-biphenylyl-6-chloro-5-formyl-hex-5-enoic acid methyl ester 6-(4'-Biphenylyl)-6-keto-hexanoic acid (5 g) methyl ester was dissolved in DMF (30 mL) and the solution added to a solution of $POCl_3$ (1 mL) in DMF (5 mL) cooled to 0° C. The reaction was stirred for 15 minutes at 0° C., warmed to room temperature for 2 hours. Water was added. The product was extracted with EtOAc. Chromatography on silica gel isolated the desired 6-(4'-biphenylyl)-6-chloro-5-formyl-hex-5-enoic acid methyl ester, 800 mg, which was identified NMR and IR spectra.

(Step B) 6-(4'-biphenylyl)-6-chloro-5-carboxy-hex-5-enoic acid methyl ester 12

6-(4'-Biphenylyl)-6-chloro-5-formyl-hex-5-enoic acid methyl ester (1 g) was dissolved in t-BuOH (75 mL). A solution of $NaClO_2$ (2.42 g) and $NaH_2PO_4$ (2.42 g) in 25 mL $H_2O$ was added dropwise. The solution was stirred for 16 hours. The methanol was removed in vacuo. The solution was acidified (3N HCl) and the product ester 12 extracted with EtOAc. 1 g, 95%. NMR and IR spectra of 12 were obtained.

(STEP C) 6-(4'-biphenylyl)hex-5-ynoic acid 13

6-(4'-Biphenylyl)-6-chloro-5-carboxy-hex-5-enoic acid methyl ester (500 mg) was dissolved in 2 mL quinoline. Eighty-eight milligrams Cu powder was added and the solution heated at 140° for 4 hours. The solution was diluted with citric acid (20% aqueous) and extracted with ethyl acetate. After drying ($Na_2SO_4$) and concentration the product was isolated by chromatography and hydrolyzed by treatment in methanol (10 mL) with 0.1 N NaOH (5 mL). Acidification precipitated the product 13 (100 mg), m.p. 95°-96°.

C: 81.81; H: 6.06; calc. C: 81.74; H: 6.18; observed.

Corresponding octenoic and decenoic acids are prepared using appropriate starting materials in the Example 11 process.

Claims to the invention follow.

What is claimed is:

1. A pharmaceutical composition useful for treating asthma, or treating or inhibiting blood platelet aggregation in humans containing an effective amount of a compound having the formula

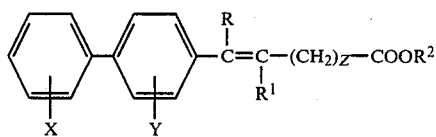

I wherein
R is H or $C_1$-$C_4$ alkyl, $C_1$-$C_4$ alkoxy or hydroxy,
$R^1$ is H or $C_1$-$C_4$ alkyl, $C_1$-$C_4$ alkoxy or hydroxy,
$R^2$ is
(i) hydrogen,
(ii) $C_1$-$C_6$ alkyl,
(iii)

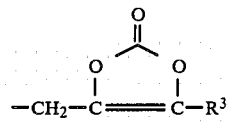

II wherein
$R^3$ is $C_1$-$C_6$ alkyl or aryl or
(iv)

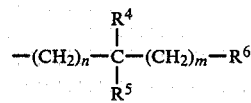

III wherein
n is 0, 1, 2, or 3;
m is 0, 1, 2, or 3;
$R^4$ and $R^5$ are individually H or alkyl of 1 to 3 carbon atoms and;
$R^6$ is selected from the group consisting of
(A) a monocyclic or bicyclic heterocyclic radical containing from 3 to 12 nuclear carbon atoms and 1 or 2 nuclear hetero atoms selected from N and S with at least one being N, and with each ring in the said heterocyclic radical containing 5 to 6 members and
(B) the radical $X^1$—$R^7$ wherein $X^1$ is —O—, —S—, or —NH— and $R^7$ contains up to 21 carbon atoms and is (1) hydrocarbon radical or (2) an acyl radical of an organic acyclic or monocyclic carboxylic acid containing not more than 1 hetero atom in the ring,
Y is H, halo, hydroxy, $C_1$-$C_4$ alkoxy or azide,
X is H, halo, hydroxy, $C_1$-$C_4$ alkoxy or azide, and
Z is 3, 5, or 7,
and pharmaceutically acceptable salts thereof.

2. A method for treating asthma, or treaing or inhibiting blood platelet aggregation in humans by administering an effective amount of a compound having the formula of the compound in the composition in claim 1.

3. A composition of claim 1 wherein Z is 3 and $R^2$ is H.

4. A composition of claim 2 wherein R is $C_1$-$C_4$ alkyl.

5. A composition of claim 2 wherein $R^1$ is $C_1$-$C_4$ alkoxy or hydroxy.

6. A composition of claim 2 herein $R^1$ H, R is H, and X and Y are H.

7. The cis isomer of the compound in the composition of claim 6.

8. The trans isomer of the compound in the composition of claim 6.

9. A process for preparing compounds of Formula I, claim 1 which comprises (a) reacting a compound of the formula

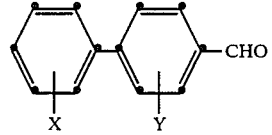

with a compound of the formula $Ph_3P=CH-(CH_2)_4-COOH$ to obtain an intermediate of the formula
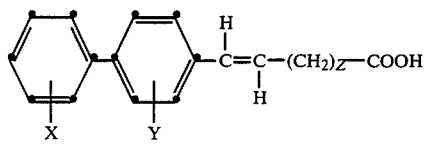
II
and esterifying said intermediate to obtain a compound of Formula I where R, $R^1$ and $R^2$ is $C_1$–$C_6$ alkyl or (b) dehydrating a compound of the formula
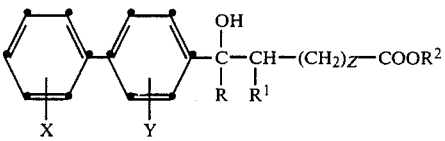
10. The process of claim 9 wherein Z is 3.
11. A process for preparing compounds of claim 8 by the reduction of a compound of the formula:
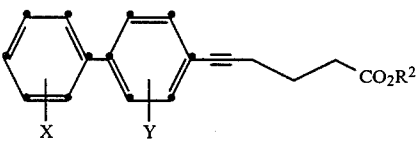
III
* * * * *